US 8,889,904 B2

(12) United States Patent
Shaver et al.

(10) Patent No.: US 8,889,904 B2
(45) Date of Patent: Nov. 18, 2014

(54) PROCESSES FOR PRODUCING ACETIC ACID

(75) Inventors: Ronald David Shaver, Houston, TX (US); Mark O. Scates, Houston, TX (US); Raymond J. Zinobile, Houston, TX (US)

(73) Assignee: Celanese International Corporation, Dallas, TX (US)

( * ) Notice: Subject to any disclaimer, the term of this patent is extended or adjusted under 35 U.S.C. 154(b) by 416 days.

(21) Appl. No.: 13/109,348

(22) Filed: May 17, 2011

(65) Prior Publication Data
US 2011/0288333 A1  Nov. 24, 2011

Related U.S. Application Data

(60) Provisional application No. 61/345,833, filed on May 18, 2010.

(51) Int. Cl.
C07C 51/42 (2006.01)
C07C 51/44 (2006.01)
C07C 51/48 (2006.01)

(52) U.S. Cl.
CPC ............... C07C 51/44 (2013.01); C07C 51/48 (2013.01)
USPC ...................................... 562/608

(58) Field of Classification Search
None
See application file for complete search history.

(56) References Cited

U.S. PATENT DOCUMENTS

| 3,769,329 | A | 10/1973 | Paulik et al. |
| 5,001,259 | A | 3/1991 | Smith et al. |
| 5,026,908 | A | 6/1991 | Smith et al. |
| 5,144,068 | A | 9/1992 | Smith et al. |
| 5,625,095 | A | 4/1997 | Miura et al. |
| 5,756,836 | A | 5/1998 | Shimizu et al. |
| 6,143,930 | A | 11/2000 | Singh et al. |
| 6,339,171 | B1 * | 1/2002 | Singh et al. ............... 562/519 |
| 7,208,625 | B1 | 4/2007 | Wang et al. |
| 7,223,883 | B2 | 5/2007 | Picard et al. |

(Continued)

FOREIGN PATENT DOCUMENTS

| CN | 101391946 | 3/2009 |
| EP | 0161874 A1 | 11/1985 |
| JP | 2007-284404 A | 11/2007 |

OTHER PUBLICATIONS

International Preliminary Report on Patentability mailed Aug. 10, 2012 in corresponding International Application No. PCT/US2011/036765.

(Continued)

*Primary Examiner* — Karl J Puttlitz

(57) ABSTRACT

Processes for the reduction and/or removal of permanganate reducing compounds (PRC'S) formed by the carbonylation of methanol in the presence of a Group VIII metal carbonylation catalyst to produce acetic acid are disclosed. More specifically, processes for reducing and/or removing PRC's or their precursors from intermediate streams during the formation of acetic acid by said carbonylation processes are disclosed. In particular, processes in which a low boiling overhead vapor stream from a light ends column is subjected to a distillation to obtain an overhead that is subjected to an extraction to selectively remove and/or reduce PRC's from the process is disclosed. The processes include steps of recycling one or more return streams derived from the distillation step and/or the extraction step to a light ends column and/or a drying column in order to improve water control in the overall reaction system.

28 Claims, 2 Drawing Sheets

(56) References Cited

U.S. PATENT DOCUMENTS

| | | | |
|---|---|---|---|
| 7,223,886 | B2 | 5/2007 | Scates et al. |
| 7,271,293 | B2 | 9/2007 | Trueba et al. |
| 7,524,988 | B2 | 4/2009 | Harris et al. |
| 7,855,306 | B2 | 12/2010 | Zinobile et al. |
| 7,884,237 | B2 | 2/2011 | Shaver |
| 7,989,659 | B2 | 8/2011 | Powell et al. |
| 8,207,377 | B2 | 6/2012 | Zinobile et al. |
| 8,501,990 | B2 | 8/2013 | Zinobile et al. |
| 2006/0247266 | A1 | 11/2006 | Yamada et al. |
| 2006/0247466 | A1* | 11/2006 | Zinobile et al. ............ 562/517 |

OTHER PUBLICATIONS

International Search Report and Written Opinion for PCT/US2011/036765, mailed Sep. 28, 2011. 13 pages.

International Preliminary Report on Patentability mailed Jan. 29, 2013 in corresponding International Application No. PCT/US2011/36765.

Watson, Derrick J., "The CativaTM Process for the Production of Acetic Acid," Catalysis of Organic Reaction, 1998, 75, pp. 369-380.

Office Action for corresponding Chinese Appl. No. 201180032069.7 dated Mar. 5, 2014.

* cited by examiner

PROCESSES FOR PRODUCING ACETIC ACID

CROSS REFERENCE TO RELATED APPLICATIONS

This application claims priority to U.S. Provisional App. No. 61/345,833, filed on May 18, 2010, the entirety of which is incorporated herein by reference.

FIELD OF THE INVENTION

This invention relates to processes for producing acetic acid and, in particular, to improved processes for reducing and/or removing permanganate reducing compounds formed during the carbonylation of methanol in the presence of a Group VIII metal carbonylation catalyst to produce acetic acid.

BACKGROUND OF THE INVENTION

Among currently employed processes for synthesizing acetic acid, one of the most useful commercially is the catalyzed carbonylation of methanol with carbon monoxide as taught in U.S. Pat. No. 3,769,329, incorporated herein by reference in its entirety. The carbonylation catalyst contains rhodium, either dissolved or otherwise dispersed in a liquid reaction medium or supported on an inert solid, along with a halogen-containing catalyst promoter as exemplified by methyl iodide. The rhodium can be introduced into the reaction system in any of many forms. Likewise, because the nature of the halide promoter is not generally critical, a large number of suitable promoters, most of which are organic iodides, may be used. Most typically and usefully, the reaction is conducted by continuously bubbling carbon monoxide gas through a liquid reaction medium in which the catalyst is dissolved.

An improvement in the prior art process for the carbonylation of an alcohol to produce the carboxylic acid having one carbon atom more than the alcohol in the presence of a rhodium catalyst is disclosed in U.S. Pat. Nos. 5,001,259; 5,026,908; and 5,144,068; and EP0161874, the entireties of which are incorporated herein by reference. As disclosed therein, acetic acid is produced from methanol in a reaction medium containing methyl acetate (MeAc), methyl halide, especially methyl iodide (MeI), and rhodium present in a catalytically effective concentration. These patents disclose that catalyst stability and the productivity of the carbonylation reactor can be maintained at high levels, even at very low water concentrations, i.e., 4 weight percent or less, (despite the conventional practice of maintaining approximately 14-15 wt. % water) by maintaining in the reaction medium, along with a catalytically effective amount of rhodium, at least a finite concentration of water, e.g., about 0.1 wt. %, and a specified concentration of iodide ions over and above the iodide ion that is present as hydrogen iodide. This iodide ion is a simple salt, with lithium iodide being preferred. The patents teach that the concentration of methyl acetate and iodide salts are significant parameters in affecting the rate of carbonylation of methanol to produce acetic acid, especially at low reactor water concentrations. By using relatively high concentrations of the methyl acetate and iodide salt, a high degree of catalyst stability and reactor productivity is achieved even when the liquid reaction medium contains water in finite concentrations as low as about 0.1 wt. %. Furthermore, the reaction medium employed improves the stability of the rhodium catalyst, i.e., resistance to catalyst precipitation, especially during the product recovery steps of the process. In these steps, distillation for the purpose of recovering the acetic acid product tends to remove from the catalyst the carbon monoxide, which in the environment maintained in the reaction vessel, is a ligand with stabilizing effect on the rhodium.

It has been found that although a low water carbonylation process for producing acetic acid reduces such by-products as carbon dioxide, hydrogen, and propionic acid, the amount of other impurities, present generally in trace amounts, can be increased by a low water carbonylation process, and the quality of acetic acid sometimes suffers when attempts are made to increase the production rate by improving catalysts, or modifying reaction conditions.

These trace impurities affect quality of acetic acid, especially when they are recirculated through the reaction process, which, among other things, can result in the build up over time of these impurities. The impurities that decrease the permanganate time of the acetic acid, a quality test commonly used in the acetic acid industry, include carbonyl compounds and unsaturated carbonyl compounds. As used herein, the phrase "carbonyl" is intended to mean compounds that contain aldehyde or ketone functional groups, which compounds may or may not possess unsaturation. See Catalysis of Organic Reaction, 75, 369-380 (1998), for further discussion on impurities in a carbonylation process.

Carbonyl impurities, such as acetaldehyde, that are formed during the carbonylation of methanol may react with iodide catalyst promoters to form multi-carbon alkyl iodides, e.g., ethyl iodide, propyl iodide, butyl iodide, pentyl iodide, hexyl iodide, and the like. It is desirable to remove multi-carbon alkyl iodides from the reaction product because even small amounts of these impurities in the acetic acid product tend to poison the catalyst used in the production of vinyl acetate, a product commonly produced from acetic acid. Thus, the present invention may also lead to reduction or removal of multi-carbon alkyl iodides, in particular $C_2$-$C_{12}$ alkyl iodide compounds. Accordingly, because many impurities originate with acetaldehyde, it is a primary objective to remove carbonyl impurities, notably acetaldehyde, from the process so as to reduce the multi-carbon alkyl iodide content.

Conventional techniques to remove such impurities include treating the acetic acid product streams with oxidizers, ozone, water, methanol, activated-carbon, amines, and the like. Such treatments may or may not be combined with distillation of the acetic acid. The most typical purification treatment involves a series of distillations of the final product. It is also known to remove carbonyl impurities from organic streams by treating the organic streams with an amine compound such as hydroxylamine, which reacts with the carbonyl compounds to form oximes, followed by distillation to separate the purified organic product from the oxime reaction products. However, the additional treatment of the final product adds cost to the process, and distillation of the treated acetic acid product can result in additional impurities being formed.

While it is possible to obtain acetic acid of relatively high purity, the acetic acid product formed by the low-water carbonylation process and purification treatment described above frequently remains somewhat deficient with respect to the permanganate time due to the presence of small proportions of residual impurities. Because a sufficient permanganate time is an important commercial test, which the acid product may be required to meet to be suitable for many uses, the presence of impurities that decrease permanganate time is objectionable. Moreover, it has not been economically or commercially feasible to remove minute quantities of these impurities from the acetic acid by distillation because some of the impurities have boiling points close to that of the acetic acid product or halogen-containing catalyst promoters, such as methyl iodide. It has thus become important to identify economically viable methods of removing impurities elsewhere in the carbonylation process without contaminating the final product or adding unnecessary costs.

The art has disclosed that carbonyl impurities present in the acetic acid product streams generally concentrate in the overhead from the light ends column. Accordingly, the light ends column overhead has been treated with an amine compound (such as hydroxylamine), which reacts with the carbonyl compounds to form derivatives that can be more easily separated from the remaining overhead by distillation, resulting in an acetic acid product with improved permanganate time.

It has been disclosed in U.S. Pat. Nos. 6,143,930 and 6,339,171 that it is possible to significantly reduce undesirable impurities in the acetic acid product by performing a multistage purification on the light ends column overhead. These patents disclose a purification process in which the light ends overhead is distilled twice, in each case taking the acetaldehyde overhead and returning a methyl iodide rich residuum to the reactor. The acetaldehyde-rich distillate obtained after the two distillation steps is optionally extracted with water to remove the majority of the acetaldehyde for disposal, leaving a significantly lower acetaldehyde concentration in the raffinate that is recycled to the reactor. U.S. Pat. Nos. 6,143,930 and 6,339,171 are incorporated herein by reference in their entirety.

In addition, it has been disclosed in US20060247466, the entirety of which is incorporated herein by reference, that it is possible to reduce undesirable impurities in the acetic acid product by subjecting the light ends overhead to a single distillation to obtain an overhead that is subjected to an extraction to selectively remove and/or reduce permanganate reducing compounds (PRC's).

U.S. Pat. No. 7,223,886, the entirety of which is incorporated herein by reference, discloses a method for reducing the formation of alkyl iodides and $C_{3-8}$ carboxylic acids by removing PRC's from the light phase of the condensed light ends overhead stream, including (a) distilling the light phase to yield a PRC enriched overhead stream; and (b) extracting the overhead stream with water in at least two consecutive stages and separating therefrom one or more aqueous streams containing PRC's.

While the above-described processes have been successful in reducing and/or removing carbonyl impurities from the carbonylation system and for the most part controlling acetaldehyde levels and permanganate time problems in the final acetic acid product, further improvements can still be made. Accordingly, there remains a need for alternative processes to improve the efficiency of acetaldehyde removal. The present invention provides one such alternative solution.

SUMMARY OF THE INVENTION

This invention relates to processes for the production of acetic acid (HOAc) and, in particular, improved processes for the reduction and/or removal of permanganate reducing compounds (PRC's) and alkyl iodides formed by the carbonylation of methanol in the presence of a Group VIII metal carbonylation catalyst to produce acetic acid. More specifically, this invention relates to improved processes for reducing and/or removing PRC's or their precursors from intermediate streams during the formation of acetic acid by the carbonylation processes. The processes of the invention desirably minimize acetic acid recycle to the reactor, thereby reducing the load on the reactor and separation system, increasing production capability, debottlenecking the separation system and decreasing utilities and the need for cooling water. In addition, the processes desirably provide an efficient means for controlling the amount of water in the reaction system, also resulting in reduced load on the reactor and improved overall efficiency. An additional benefit of the processes of the invention is that they provide improved flexibility in controlling the water load between the light ends column and the drying column of the separation system.

In one embodiment, the invention is to a process for removing PRC's from a crude acetic acid composition comprising acetic acid and one or more PRC's, the process comprising the steps of: separating the crude acetic acid composition in a light ends column into a PRC enriched stream and an acetic acid stream; separating the PRC enriched stream into an aqueous phase and an organic phase; separating the aqueous phase in a PRC removal system (PRS) distillation column into an overhead stream and a bottoms stream; and directing a first return stream comprising an aliquot portion of the bottoms stream to the light ends column. The process may further comprise the step of combining the aliquot portion of the bottoms stream with one or more process streams to form the first return stream. Preferably, the process further comprises the step of extracting at least a portion of the overhead stream with an extraction medium to form a PRC extracted stream and a raffinate, wherein the first return stream further comprises at least a portion of the raffinate. Optionally, the process further comprises the steps of distilling the acetic acid stream in a drying column to form a water stream and an acetic acid product stream; and directing a second return stream comprising an aliquot portion of the bottoms stream to the drying column. The second return stream optionally comprises the aliquot portion of the bottoms stream and a reflux stream. In one aspect, the second return stream further comprises an aliquot portion of the raffinate.

In one aspect, the process further comprises the steps of: distilling the acetic acid stream in a drying column to form a water stream and an acetic acid product stream; and directing a second return stream comprising an aliquot portion of the bottoms stream to the drying column. The second return stream optionally comprises the aliquot portion of the bottoms stream and a reflux stream. Optionally, the process further comprises the step of: extracting at least a portion of the overhead stream with an extraction medium to form a PRC extracted stream and a raffinate, wherein the second return stream further comprises a portion of the raffinate.

In another aspect, the process further comprises the steps of: extracting at least a portion of the overhead stream with an extraction medium to form a PRC extracted stream and a raffinate, distilling the acetic acid stream in a drying column to form a water stream and an acetic acid product stream; and directing a second return stream comprising an aliquot portion of the raffinate to the drying column.

In another embodiment, the invention is directed to a process for removing PRC's from a crude acetic acid composition comprising acetic acid and one or more PRC's, the process comprising the steps of: separating the crude acetic acid composition in a light ends column into a PRC enriched stream and an acetic acid stream; separating the PRC enriched stream into an aqueous phase and an organic phase; separating the aqueous phase in a PRS distillation column into an overhead stream and a bottoms stream; extracting at least a portion of the overhead stream with an extraction medium in an extraction unit to form a PRC extracted stream and a raffinate; and directing a first return stream comprising an aliquot portion of the raffinate to the light ends column. The process optionally further comprises the step of combining the aliquot portion of the raffinate with one or more process streams to form the first return stream. Optionally, at least a portion of the bottoms stream is directed to the light ends column, optionally as part of the first return stream. In one aspect, the process further comprises the steps of: distilling the acetic acid stream in a drying column to form a water stream and an acetic acid product stream; and directing a second return stream comprising a second aliquot portion of the raffinate to the drying column. In this aspect, at least a portion of the bottoms stream optionally is directed to the light ends column, optionally as part of the first return stream. In one aspect, at least a portion of the bottoms stream may be directed to the drying column, optionally as part of the second return stream. In another aspect, the process further comprises the steps of distilling the acetic acid stream in a drying column to form a water stream and an acetic acid product stream; and directing a second return stream comprising an aliquot portion of the bottoms stream to the drying column. The second return stream may comprise the aliquot portion of the bottoms stream and a reflux stream. Optionally, the first return stream further comprises an aliquot portion of the bottoms stream.

In another embodiment, the invention is to a process for removing PRC's from a crude acetic acid composition comprising acetic acid and one or more PRC's, the process comprising the steps of: separating the crude acetic acid composition in a light ends column into a PRC enriched stream and an acetic acid stream; separating the PRC enriched stream into an aqueous phase and an organic phase; separating the aqueous phase in a PRS distillation column into an overhead stream and a bottoms stream; distilling the acetic acid stream in a drying column to form a water stream and an acetic acid product stream; and directing a first return stream comprising an aliquot portion of the bottoms stream to the drying column. Optionally, the process further comprises the steps of: extracting at least a portion of the overhead stream with an extraction medium to form a PRC extracted stream and a raffinate, wherein the first return stream further comprises an aliquot portion of the raffinate. The process may further comprise the steps of: extracting at least a portion of the overhead stream with an extraction medium to form a PRC extracted stream and a raffinate; and directing a second return stream comprising an aliquot portion of the raffinate to the light ends column. In this aspect, the first return stream may further comprise a portion of the raffinate.

In another embodiment, the invention is directed to a process for the reduction and/or removal of PRC's formed in the carbonylation of a carbonylatable reactant to produce a carbonylation product comprising acetic acid, comprising the steps of: separating the carbonylation product in a first separation unit to form a first overhead stream comprising acetic acid and a first bottoms stream comprising catalyst; distilling the first overhead stream in a second separation unit to form a crude acetic acid product and a second overhead stream comprising methyl iodide, water, acetic acid, methyl acetate, and at least one PRC yield; condensing the second overhead stream and biphasically separating it to form a condensed heavy liquid phase and a condensed light liquid phase; distilling the condensed light liquid phase in a third separation unit to form a third overhead stream and a third bottoms stream, wherein the third overhead stream is enriched with PRC's with respect to the condensed light liquid phase; and directing a first return stream comprising an aliquot portion of the third bottoms stream to the second separation unit. The process may further comprise the steps of condensing the third overhead stream and extracting the resulting condensed stream with water to obtain an aqueous acetaldehyde stream comprising PRC and a raffinate comprising methyl iodide, wherein the first return stream further comprises an aliquot portion of the raffinate, and optionally the steps of distilling the crude acetic acid product in a fourth separation unit to form a fourth overhead stream comprising water and a fourth bottoms stream comprising acetic acid product; and directing a second return stream comprising an aliquot portion of the third bottoms stream to the fourth separation unit. In one aspect, the process further comprises the steps of distilling the crude acetic acid product in a fourth separation unit to form a fourth overhead stream comprising water and a fourth bottoms stream comprising acetic acid product; and directing a second return stream comprising an aliquot portion of the third bottoms stream to the fourth separation unit.

In another embodiment, the invention is directed to a process for the reduction and/or removal of PRC's formed in the carbonylation of a carbonylatable reactant to produce a carbonylation product comprising acetic acid, comprising the steps of: separating the carbonylation product in a first separation unit to form a first overhead stream comprising acetic acid and a first bottoms stream comprising catalyst; distilling the first overhead stream in a second separation unit to form a crude acetic acid product and a second overhead stream comprising methyl iodide, water, acetic acid, methyl acetate, and at least one PRC yield; condensing the second overhead stream and biphasically separating it to form a condensed heavy liquid phase and a condensed light liquid phase; distilling the condensed light liquid phase in a third separation unit to form a third overhead stream and a third bottoms stream, wherein the third overhead stream is enriched with PRC's with respect to the condensed light liquid phase; condensing the third overhead stream and extracting the resulting condensed stream with water to obtain an aqueous acetaldehyde stream comprising PRC and a raffinate comprising methyl iodide; and directing a first return stream comprising an aliquot portion of the raffinate to the second separation unit. The process optionally further comprises the steps of distilling the crude acetic acid product in a fourth separation unit to form a fourth overhead stream comprising water and a fourth bottoms stream comprising acetic acid product; and directing a second return stream comprising an aliquot portion of the third bottoms stream to the fourth separation unit.

In another embodiment, the invention is to a process for the reduction and/or removal of PRC's formed in the carbonylation of a carbonylatable reactant to produce a carbonylation product comprising acetic acid, comprising the steps of: separating the carbonylation product in a first separation unit to form a first overhead stream comprising acetic acid and a first bottoms stream comprising catalyst; distilling the first overhead stream in a second separation unit to form a crude acetic acid product and a second overhead stream comprising methyl iodide, water, acetic acid, methyl acetate, and at least one PRC yield; condensing the second overhead stream and biphasically separating it to form a condensed heavy liquid phase and a condensed light liquid phase; distilling the condensed light liquid phase in a third separation unit to form a third overhead stream and a third bottoms stream, wherein the third overhead stream is enriched with PRC's with respect to the condensed light liquid phase; distilling the crude acetic acid product in a fourth separation unit to form a fourth overhead stream comprising water and a fourth bottoms stream comprising purified acetic acid; and directing a first return stream comprising an aliquot portion of the third bottoms stream to the fourth separation unit. The process optionally further comprises the steps of condensing the third overhead stream and extracting the resulting condensed stream with water to obtain an aqueous acetaldehyde stream comprising PRC and a raffinate comprising methyl iodide, and directing a second return stream comprising an aliquot portion of the raffinate to the second separation unit.

In another embodiment, the invention is directed to a process for removing PRC's from a crude acetic acid composition comprising acetic acid and one or more PRC's, the process comprising the steps of: separating the crude acetic acid composition in a light ends column into a PRC enriched stream and an acetic acid stream; separating at least a portion of the acetic acid stream in a drying column to form a water stream and an acetic acid product stream; separating the PRC enriched stream into an aqueous phase and an organic phase; separating the aqueous phase in a PRS distillation column into an overhead stream and a bottoms stream; extracting at least a portion of the overhead stream with an extraction medium to form a PRC extracted stream and a raffinate; directing a first return stream comprising an aliquot portion of the bottoms stream to the light ends column; directing at least a portion of the raffinate to the light ends column, optionally as part of the first return stream; and directing a second return stream comprising an aliquot portion of the bottoms stream to the drying column. The process optionally further comprises the step of directing a portion of the raffinate to the drying column, optionally as part of the second return stream.

For those embodiments that include an extraction step, the extraction medium optionally comprises water and/or dimethyl ether. Preferably, dimethyl ether is present in the extracting step, whether separately added or formed in situ, in an amount sufficient to reduce methyl iodide concentration in the PRC extracted stream to an amount less than 1.8 wt. %, e.g., less than 1.5 wt. % or from 0.5 to 1.8 wt. %.

BRIEF DESCRIPTION OF THE DRAWINGS

The present invention will be better understood in view of the appended non-limiting figures, wherein.

DETAILED DESCRIPTION OF THE INVENTION

Introduction

Figure 1:
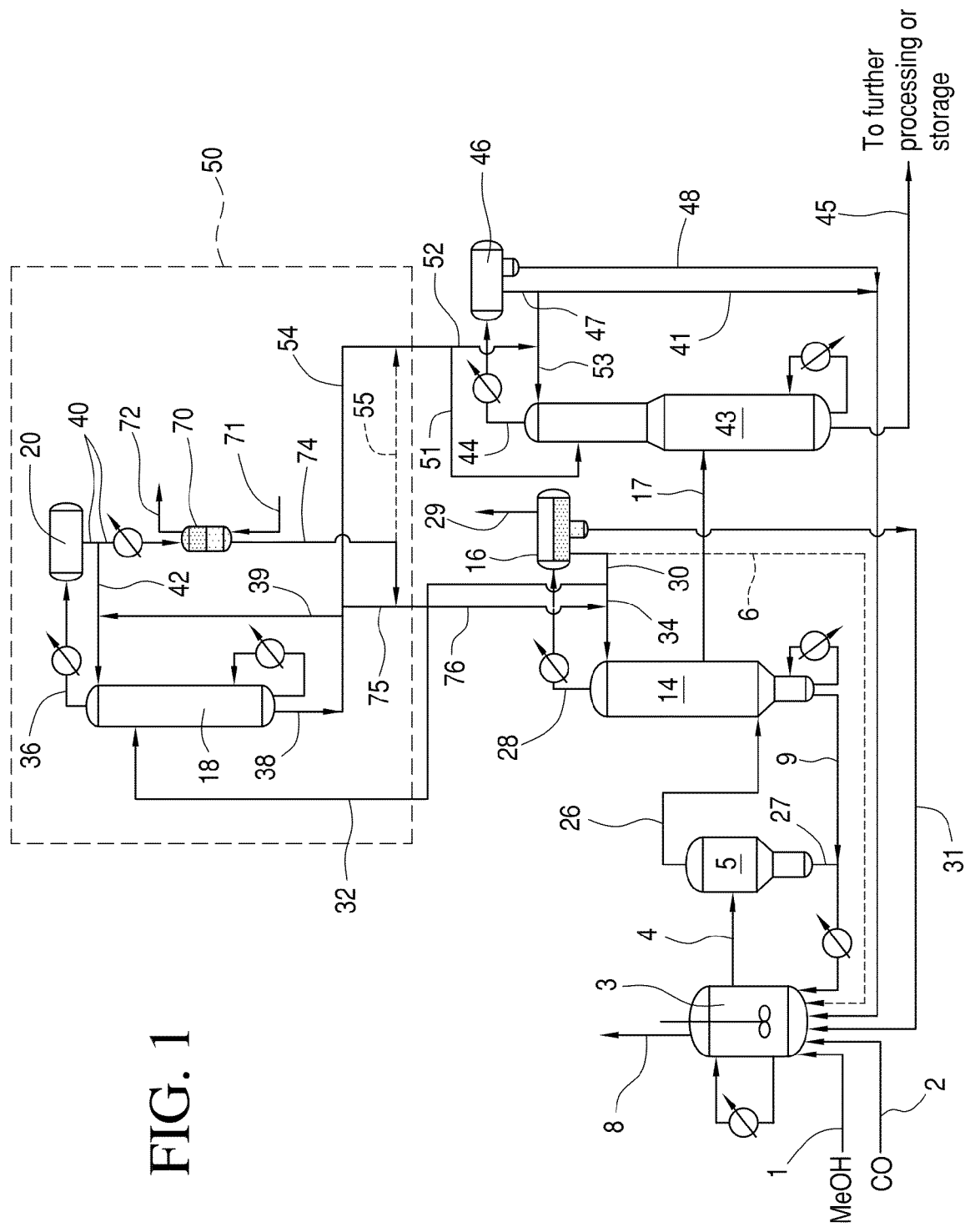
FIG. 1 illustrates an exemplary acetic acid reaction system and separation scheme according to one embodiment of the present invention.

This invention relates to processes for the production of acetic acid and, in particular, to improved processes for the reduction and/or removal of permanganate reducing compounds (PRC's) formed during the carbonylation of methanol in the presence of a Group VIII metal carbonylation catalyst. PRC's, may include, for example, compounds such as acetaldehyde (AcH), acetone, methyl ethyl ketone, butyraldehyde, crotonaldehyde, 2-ethyl crotonaldehyde, and 2-ethyl butyraldehyde and the like, and the aldol condensation products thereof. More specifically, this invention relates to improved processes for reducing and/or removing PRC's or their precursors from an acetic acid separation system that is used to purify a crude acetic acid product.

In a preferred embodiment, the present invention relates to a process in which a crude acetic acid composition, preferably derived from a carbonylation reactor or flash vessel, is separated in a light ends column into a PRC enriched stream and an acetic acid stream, e.g., an acetic acid side stream. The PRC enriched stream is then separated into an aqueous phase and an organic phase, preferably in a phase separation unit. The portion of the resulting aqueous phase is then directed to a PRC removal system (PRS) where it is separated in a PRS distillation column into an overhead stream and a bottoms stream. The remaining portion of the aqueous stream may be refluxed to the light ends column. A return stream comprising an aliquot portion of the bottoms stream is then returned to the light ends column, preferably to the top of the light ends column, for further processing. In one embodiment, directing a portion or all of the return stream into a reflux of the light ends column. In one embodiment, a portion or all of the return stream may be refluxed to light ends column. In one embodiment, the bottoms stream is exclusively returned to the light ends column and no return stream is directed from the PRS elsewhere in the system.

The PRS may further include a step of extracting at least a portion of the PRS distillation column overhead stream with an extraction medium to form a PRC extracted stream and a raffinate. In this aspect, the return stream may further comprise at least a portion, e.g., an aliquot portion, or the entirety of the raffinate.

In another embodiment, the process includes the step of distilling an acetic acid stream derived from a light ends column in a drying column to form a water stream and an acetic acid product stream. A second return stream comprising an aliquot portion of the bottoms stream from the PRS distillation column is directed to the drying column, preferably to the top of the drying column. In one embodiment, the bottoms stream returned to the separation system is exclusively returned as the second return stream to the drying column and no return stream is directed from the PRS to the light ends column. Additionally or alternatively, the second return stream may comprise an aliquot portion of the raffinate from the PRS extraction unit.

In one embodiment, the bottoms stream and optionally the raffinate streams are directed either to the light ends column and/or drying column, but are not directed to the reactor or any recycle lines that are fed to the reactor.

Among other advantages, the processes of the invention beneficially provide efficient means for reducing and/or removing PRC's while improving water control in the overall acetic acid production system. This preferably results in smaller reactor and flash vessel size allowing for reduced capital expenditure. The processes of the invention preferably also reduce unnecessary acetic acid recycle to the reactor, thereby reducing the load on the separation system, resulting in increased production capability. In addition, maintaining desired water control is preferred to establish a stable acetic acid reaction system, and particularly for ensuring an efficient separation scheme. Additional advantages include, but are not limited to, lower energy usage and reduced equipment and associated costs.

Acetic Acid Production Systems

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The purification processes of the present invention are useful in carbonylation processes that use methanol and/or methyl acetate (MeAc), methyl formate or dimethyl ether, or mixtures thereof, to produce acetic acid in the presence of a Group VIII metal catalyst, such as rhodium, and a halogen-containing catalyst promoter. A particularly useful process is the low water rhodium-catalyzed carbonylation of methanol to acetic acid as exemplified in U.S. Pat. No. 5,001,259.

Generally, the rhodium component of the catalyst system is believed to be present in the form of a coordination compound of rhodium with a halogen component providing at least one of the ligands of such coordination compound. In addition to the coordination of rhodium and halogen, it is also believed that carbon monoxide will coordinate with rhodium. The rhodium component of the catalyst system may be provided by introducing into the reaction zone rhodium in the form of rhodium metal, rhodium salts such as the oxides, acetates, iodides, carbonates, hydroxides, chlorides, etc., or other compounds that result in the formation of a coordination compound of rhodium in the reaction environment.

The halogen-containing catalyst promoter of the catalyst system consists of a halogen compound comprising an organic halide. Thus, alkyl, aryl, and substituted alkyl or aryl halides can be used. Preferably, the halogen-containing catalyst promoter is present in the form of an alkyl halide. Even more preferably, the halogen-containing catalyst promoter is present in the form of an alkyl halide in which the alkyl radical corresponds to the alkyl radical of the feed alcohol, which is being carbonylated. Thus, in the carbonylation of methanol to acetic acid, the halide promoter will include methyl halide, and more preferably methyl iodide.

The liquid reaction medium employed may include any solvent compatible with the catalyst system and may include pure alcohols, or mixtures of the alcohol feedstock and/or the desired carboxylic acid and/or esters of these two compounds. A preferred solvent and liquid reaction medium for the low water carbonylation process contains the desired carboxylic acid product. Thus, in the carbonylation of methanol to acetic acid, a preferred solvent system contains acetic acid.

Water is contained in the reaction medium but desirably at low concentrations well below that which has heretofore been thought practical for achieving sufficient reaction rates. It has previously been taught, e.g., in U.S. Pat. No. 3,769,329, that in rhodium-catalyzed carbonylation reactions of the type set forth in this invention, the addition of water exerts a beneficial effect upon the reaction rate. Thus, commercial operations are commonly run at water concentrations of at least about 14 wt. %. Accordingly, it has been quite unexpected that reaction rates substantially equal to and above reaction rates obtained with such comparatively high levels of water concentration can be achieved with water concentrations below 14 wt. % and as low as about 0.1 wt. %, e.g., from 0.1 wt. % to 14 wt. %, from 0.2 wt. % to 10 wt. % or from 0.25 wt. % to 5 wt. %, based on the total weight of the reaction medium.

In accordance with the carbonylation process most useful to manufacture of acetic acid according to the present invention, the desired reaction rates are obtained even at low water concentrations by maintaining in the reaction medium an ester of the desired carboxylic acid and an alcohol, desirably the alcohol used in the carbonylation, and an additional iodide ion that is over and above the iodide ion that is present as hydrogen iodide. A desired ester is methyl acetate. The additional iodide ion is desirably an iodide salt, with lithium iodide (LiI) being preferred. It has been found, as described in U.S. Pat. No. 5,001,259, that under low water concentrations, methyl acetate and lithium iodide act as rate promoters only when relatively high concentrations of each of these components are present and that the promotion is higher when both of these components are present simultaneously. The concentration of iodide ion maintained in the reaction medium of the preferred carbonylation reaction system is believed to be quite high as compared with what little prior art there is dealing with the use of halide salts in reaction systems of this sort. The absolute concentration of iodide ion content is not a limitation on the usefulness of the present invention.

The carbonylation reaction of methanol to acetic acid product may be carried out by contacting the methanol feed with gaseous carbon monoxide bubbled through an acetic acid solvent reaction medium containing the rhodium catalyst, methyl iodide (MeI) promoter, methyl acetate (MeAc), and additional soluble iodide salt, at conditions of temperature and pressure suitable to form the carbonylation product. It will be generally recognized that it is the concentration of iodide ion in the catalyst system that is important and not the cation associated with the iodide, and that at a given molar concentration of iodide the nature of the cation is not as significant as the effect of the iodide concentration. Any metal iodide salt, or any iodide salt of any organic cation, or other cations such as those based on amine or phosphine compounds (optionally, ternary or quaternary cations), can be maintained in the reaction medium provided that the salt is sufficiently soluble in the reaction medium to provide the desired level of the iodide. When the iodide is a metal salt, preferably it is an iodide salt of a member of the group consisting of the metals of Group IA and Group IIA of the periodic table as set forth in the "Handbook of Chemistry and Physics" published by CRC Press, Cleveland, Ohio, 2002-03 (83rd edition). In particular, alkali metal iodides are useful, with lithium iodide being particularly suitable. In the low water carbonylation process most useful in this invention, the additional iodide ion over and above the iodide ion present as hydrogen iodide is generally present in the catalyst solution in amounts such that the total iodide ion concentration is from about 2 to about 20 wt. % and the methyl acetate is generally present in amounts of from about 0.5 to about 30 wt. %, and the methyl iodide is generally present in amounts of from about 5 to about 20 wt. %. The rhodium catalyst is generally present in amounts of from about 200 to about 2000 parts per million (ppm).

Typical reaction temperatures for carbonylation will be from about 150° C. to about 250° C., with the temperature range of about 180° C. to about 220° C. being a preferred range. The carbon monoxide partial pressure in the reactor can vary widely but is typically from about 2 to about 30 atmospheres, e.g., from about 3 to about 10 atmospheres. Because of the partial pressure of by-products and the vapor pressure of the contained liquids, the total reactor pressure will range from about 15 to about 40 atmospheres.

An exemplary reaction and acetic acid recovery system that is used for the iodide-promoted rhodium catalyzed carbonylation of methanol to acetic acid in accordance with one embodiment of the present invention is shown in FIG. 1. As shown, a methanol-containing feed stream 1 and a carbon monoxide-containing feed stream 2 are directed to a liquid phase carbonylation reactor 3, in which the carbonylation reaction occurs to form acetic acid.

The carbonylation reactor 3 is preferably either a stirred vessel or bubble-column type vessel, with or without an agitator, within which the reacting liquid or slurry contents are maintained, preferably automatically, a predetermined level, which preferably remains substantially constant during normal operation. Into reactor 3, fresh methanol, carbon monoxide, and sufficient water are continuously introduced as needed to maintain at least a finite concentration of water, e.g., about 0.1 wt. %., in the reaction medium.

In a typical carbonylation process, carbon monoxide is continuously introduced into the carbonylation reactor, desirably below the agitator, which may be used to stir the contents. The gaseous feed preferably is thoroughly dispersed through the reacting liquid by this stirring means. A gaseous purge stream 8 desirably is vented from the reactor 3 to prevent buildup of gaseous by-products and to maintain a set carbon monoxide partial pressure at a given total reactor pressure. The temperature of the reactor may be controlled and the carbon monoxide feed is introduced at a rate sufficient to maintain the desired total reactor pressure.

The acetic acid production system preferably includes a separation system employed to recover the acetic acid and recycle catalyst solution, methyl iodide, methyl acetate, and other system components within the process. Thus, a recycled catalyst solution, such as stream 27 from flasher 5, and optionally one or more of recycle streams 6, 9, 31, 41 and 48, also are introduced into the reactor 3. Of course, one or more of the recycle streams may be combined prior to being introduced into the reactor. The separation system also preferably controls water and acetic acid content in the carbonylation reactor, as well as throughout the system, and facilitates PRC removal.

Carbonylation product is drawn off from the carbonylation reactor 3 at a rate sufficient to maintain a constant level therein and is provided to a flasher 5 via stream 4. In flasher 5, the crude product is separated in a flash separation step to obtain a volatile ("vapor") overhead stream 26 comprising acetic acid and a less volatile stream 27 comprising a catalyst-containing solution (predominantly acetic acid containing the rhodium and the iodide salt along with lesser quantities of methyl acetate, methyl iodide, and water), which preferably is recycled to the reactor, as discussed above. The vapor overhead stream 26 also comprises methyl iodide, methyl acetate, water, and PRC's. Dissolved gases exiting the reactor and entering the flasher comprise a portion of the carbon monoxide and may also contain gaseous by-products such as methane, hydrogen, and carbon dioxide. Such dissolved gases exit the flasher as part of the overhead stream. The overhead stream from flasher 5 is directed to the light ends column 14 as stream 26, where distillation yields a low-boiling overhead vapor stream 28, a purified acetic acid product that preferably is removed via a side stream 17, and a high boiling residue stream 9. Acetic acid removed via side stream 17 preferably is subjected to further purification, such as in drying column 43 for selective separation of acetic acid from water.

It has been disclosed in U.S. Pat. Nos. 6,143,930 and 6,339,171 that there is generally a higher concentration of the PRC's, and in particular acetaldehyde content, in the low-boiling overhead vapor stream exiting the light ends column than in the high-boiling residue stream exiting the column. Thus, in accordance with the present invention, low-boiling overhead vapor stream 28, containing PRC's, is subjected to additional processing in a PRS 50 to reduce and/or remove the amount of PRC's present. As shown, low-boiling overhead vapor stream 28, therefore, is condensed and directed to an overhead phase separation unit, as shown by overhead receiver decanter 16. In addition to PRC's, low-boiling overhead vapor stream 28 will typically contain methyl iodide, methyl acetate, acetic acid, and water.

Conditions are desirably maintained in the process such that low-boiling overhead vapor stream 28, once in decanter 16, will separate into a light phase and a heavy phase. Generally, low-boiling overhead vapor stream 28 is cooled to a temperature sufficient to condense and separate the condensable methyl iodide, methyl acetate, acetaldehyde and other carbonyl components, and water into two phases. A portion of stream 28 may include noncondensable gases such as carbon monoxide, carbon dioxide, hydrogen, and the like that can be vented as shown by stream 29 in FIG. 1, which may be directed to a low pressure absorber unit (not shown).

The condensed light phase in decanter 16 generally will comprise water, acetic acid, and PRC's, as well as quantities of methyl iodide and methyl acetate. The condensed heavy phase in decanter 16 will generally comprise methyl iodide, methyl acetate, and PRC's. The condensed heavy liquid phase in the decanter 16 can be conveniently recirculated, either directly or indirectly, to the reactor 3 via stream 31. For example, a portion of this condensed heavy liquid phase can be recirculated to the reactor, with a slip stream (not shown), generally a small amount, e.g., from 5 to 40 vol. %, or from 5 to 20 vol. %, of the heavy liquid phase being directed to a PRS. This slip stream of the heavy liquid phase may be treated individually or may be combined with the condensed light liquid phase stream 30 for further distillation and extraction of carbonyl impurities in accordance with one embodiment of the present invention.

Although the specific compositions of the light phase stream 30 may vary widely, some preferred compositions are provided below in Table 1.

TABLE 1

| Exemplary Light Compositions from Light Ends Overhead | | | |
|---|---|---|---|
| | conc. (Wt. %) | conc. (Wt. %) | conc. (Wt. %) |
| HOAc | 1-40 | 1-25 | 5-15 |
| Water | 50-90 | 50-80 | 60-80 |
| PRC's | <5 | <3 | <1 |
| MeI | <10 | <5 | <3 |
| MeAc | 1-50 | 1-25 | 1-15 |

As shown in FIG. 1, the light phase exits decanter 16 via stream 30. A first portion, e.g., aliquot portion, of light phase stream 30 is recycled to the top of the light ends column 14 as reflux stream 34. A second portion, e.g., aliquot portion, of light phase stream 30 is directed to the PRS, as discussed below and as shown by stream 32. A third portion, e.g., aliquot portion, of the light phase stream 30 optionally may be recycled to reactor 3 as shown by recycle stream 6, when additional water is desired or needed in reactor 3. In preferred aspects the water level is maintained in the reactor at a desired level without recycling stream 6 to reactor 3 since recycling stream 6 to the reactor undesirably will result in the recycle of acetic acid and unnecessarily increasing the load on reactor 3. Thus, the only recycle from decanter 16 to reactor 3 is through the heavy phase stream 31.

Light ends column 14 also preferably forms a residuum or bottoms stream 9, which comprises primarily acetic acid and water. Since the light ends bottoms stream 9 typically will comprise some residual catalyst, it may be beneficial to recycle all or a portion of the light ends bottoms stream 9 to reactor 3. Optionally, the light ends bottoms stream may be combined with the catalyst phase 27 from flasher 5 and returned together to reactor 3, as shown in FIG. 1.

As indicated above, in addition to the overhead phase, the light ends column 14 also forms an acetic acid side stream 17, which preferably comprises primarily acetic acid and water. In order to maintain an efficient product separation, it is important that the composition of the side stream 17 does not vary or fluctuate significantly during normal operation. The inventive separation schemes of the present invention, which employ one or more return streams from the PRS, as disclosed below, are highly effective in maintaining desirable water control in the reaction system and, as a result, in maintaining a substantially constant composition of side stream 17. In addition, the processes of the invention desirably provide the ability to control water content in the separation system, and in particular, provide improved flexibility in controlling the water balance between the light ends column 14 and the drying column 43 resulting in improved reaction system stability.

Optionally, a portion of the side stream 17 may be recirculated to the light ends column, preferably to a point below where side stream 17 was removed from light ends column, in order to improve the separation.

Since side stream 17 contains water in addition to acetic acid, side stream 17 from the light ends column 14 preferably is directed to a drying column 43, in which the acetic acid and water are separated from one another. As shown, drying column 43, separates acetic acid side stream 17 into an overhead stream 44 comprised primarily of water and a bottoms stream 45 comprised primarily of acetic acid. Overhead stream 44 preferably is cooled and condensed in a phase separation unit, e.g., decanter 46, to form a light phase and a heavy phase. As shown, a portion of the light phase is refluxed, as shown by streams 47 and 53 and the remainder of the light phase is returned to the reactor 3, as shown by stream 41. The heavy phase, which typically is an emulsion comprising water and methyl iodide, preferably is returned in its entirety to the reactor 3, as shown by stream 48, optionally after being combined with stream 41. Exemplary compositions for the light phase of the drying column overhead are provided below in Table 2.

TABLE 2

Exemplary Light Compositions from Drying Column Overhead

|      | conc. (Wt. %) | conc. (Wt. %) | conc. (Wt. %) |
|------|---------------|---------------|---------------|
| HOAc | 1-20          | 1-15          | 1-10          |
| Water| 50-90         | 60-90         | 70-90         |
| MeI  | <10           | <5            | <3            |
| MeAc | 1-20          | 1-15          | 1-10          |

The drying column bottoms stream 45 preferably comprises or consists essentially of acetic acid. In preferred embodiments, the drying column bottoms stream comprises acetic acid in an amount greater than 90 wt. %, e.g., greater than 95 wt. % or greater than 98 wt. %. Optionally, the drying column bottoms stream 45 may be further processed, e.g. by passing through an ion exchange resin, prior to being stored or transported for commercial use.

PRC Removal System (PRS)

Figure 2:
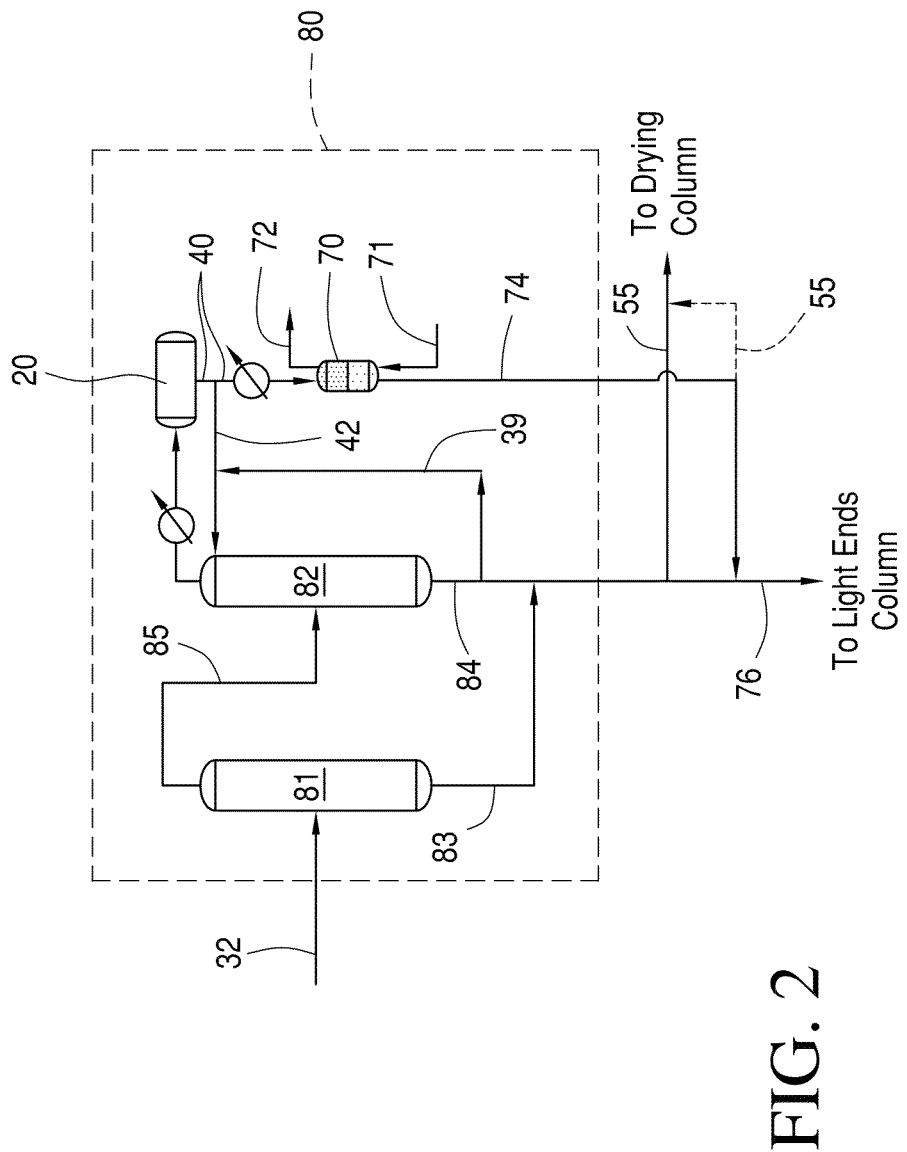
FIG. 2 illustrates an exemplary PRC removal system (PRS) according to one embodiment of the invention.

The present invention may broadly be considered as an improved process for reducing and/or removing PRC's, primarily aldehydes such as acetaldehyde, from a low-boiling overhead vapor stream of a light ends distillation column, more preferably from the condensed light phase of a low-boiling overhead vapor stream 28 from a light ends distillation column 14. Specifically, the invention relates to recycling one or more return streams from a PRS to the separation system of an acetic acid production system. Thus, no return streams from the PRS 50 are directed to the reactor 3 or to recycle lines to reactor 3. The PRS preferably includes at least one distillation column and at least one extraction column to reduce and/or remove PRC's. Although the invention is described herein with reference to FIG. 1 in terms of a PRS having a single distillation column, it should be understood that it may be similarly adapted to a multi-distillation PRC removal system, as described in U.S. Pat. No. 6,339,171. For example, as shown in FIG. 2, if two PRC distillation columns are employed, 81, 82, the bottoms streams 83, 84, from both distillation columns, separately or in combination, may be returned to either or both the light ends column and/or the drying column, as shown in exemplary PRS 80. Overhead stream 85 from first PRC distillation column 81 preferable is directed to second PRC distillation column 82, and the overhead from the second PRC distillation column preferably is extracted, as discussed above in connection with FIG. 1.

Similarly, although the PRS described and shown in FIG. 1 contains a single extraction step, it should be understood that the system may include multiple extraction stages, as described for example in U.S. Pat. No. 7,223,886 and optionally including multistage countercurrent extraction. According to various embodiments of the invention, one or more streams derived from either or both (i) the PRS distillation column and/or (ii) the PRS extraction stage, for example, may be returned to either or both (i) the light ends removal column and/or (ii) the drying column of the separation system for the acetic acid production system. For purposes of the present specification and claims, the overhead streams and overhead decanters of the light ends removal column and the drying column are considered to be part of the light ends removal column and of the drying column.

As indicated above, while either phase of the low-boiling overhead vapor stream 28, may be subsequently processed to remove the PRC's, and primarily the acetaldehyde component of the stream, in the present invention, the PRC's are removed from a portion, e.g., an aliquot portion, of the condensed light liquid phase 30, as shown by stream 32, which is directed to the PRS 50.

In accordance with the present invention, stream 32 is directed to a distillation column 18 in the PRS, which serves to form an overhead stream 36 enriched in PRC's, notably acetaldehyde, with respect to the light condensed liquid phase 30/32, but also containing methyl iodide due to the similar boiling points of methyl iodide and acetaldehyde. The overhead stream 36 is deficient of methyl acetate, methanol, and/or acetic acid (desirably all three) with respect to light condensed liquid phase 30/32 and with respect to bottoms stream 38, which is also formed by distillation column 18. Bottoms stream 38 preferably is enriched in water, acetic acid, methanol, and/or methyl acetate (desirably all four) when compared with the composition of any one of streams 30, 32 and 36.

In one embodiment, a portion, e.g., an aliquot portion, of bottoms stream 38 from PRS distillation column 18 is refluxed to the distillation column 18, as shown by stream 39. The reflux ratio of stream 39 to the remaining bottoms stream optionally is from 0.005:1 to 0.5:1, e.g., from 0.01:1 to 0.1:1. Although the compositions may vary depending on the specific PRS employed, some exemplary compositions of the PRS distillation column overhead stream 36 and bottoms stream 38 are provided in Table 3.

TABLE 3

Exemplary Overhead and Bottoms Stream Compositions for PRS Distillation Column

|       | Overhead 36 | | | Bottoms 38 | | |
|-------|-------------|--|--|------------|--|--|
|       | conc. (wt. %) | conc. (wt. %) | conc. (wt. %) | conc. (wt. %) | conc. (wt. %) | conc. (wt. %) |
| HOAc  | <3    | <1    | <0.5  | 1-40  | 1-30  | 1-20  |
| water | <15   | <10   | <5    | 50-90 | 60-90 | 70-90 |
| PRC's | 10-40 | 15-40 | 20-40 | <0.3  | <0.2  | <0.1  |
| MeI   | 50-90 | 60-90 | 60-80 | <10   | <5    | <3    |
| MeAc  | <10   | <5    | <2    | 5-50  | 5-25  | 5-15  |

In one optional embodiment, not shown, PRS distillation column 18 also forms a side stream enriched in methyl acetate, which might otherwise build up in the center of column 18 or be pushed into the overhead stream 36. This side stream allows the distillation column 18 to be operated under conditions desirable for obtaining a higher concentration of acetaldehyde in overhead stream 36 while providing a mechanism for removing methyl acetate. The side stream, comprising methyl acetate, preferably is retained in the process, and may be returned to the reactor.

In a first aspect of the invention, a first portion, e.g., an aliquot portion, of bottoms stream 38 is directed to light ends column 14 as a return stream 75 for further processing in the separation system. Optionally, the first portion of bottoms stream 38 is combined with one or more other streams, such as raffinate 74, prior to being introduced into light ends column 14 as shown in FIG. 1 and as described in greater detail below.

In a second aspect of the invention, which optionally may be combined with the above described first aspect of the invention, a second portion 54, e.g., an aliquot portion, of the bottoms stream 38 is directed to drying column 43, preferably the upper portion of drying column 43, as a return stream for further processing. The second portion 54 of bottoms stream 38 optionally may be combined with one or more other streams prior to being introduced into drying column 43. As shown in FIG. 1, the second portion 54 may be (i) added directly to the top of drying column 43 as shown by stream 51, (ii) added as stream 52 to a light phase reflux derived from drying column decanter 46 to form a combined stream 53 that is introduced into the drying column 43; or (iii) both. In additional optional embodiments, all or a portion of second portion 54 may be added directly to decanter 46 and/or be returned to reactor 3.

In embodiments that include both the first and the second aspects, the volume ratio of the amount of the PRS distillation column bottoms streams that is directed to the light ends column to the amount of the bottoms stream that is directed to the drying column may vary widely, and depends on issues such as water control, the size of the columns, the catalyst employed, the presence of impurities, and feed rate to the PRS. In a preferred aspect, a volume ratio is greater than 1:1, e.g., greater than 4:1, greater than 8:1, or greater than 10:1. In terms of ranges, the volume ratio of the amount of the PRS distillation column bottoms streams that is directed to the to the light ends column to the amount of the bottoms stream that is directed to the drying column ranges from 1:1 to 20:1, e.g., from 5:1 to 15:1, from 9:1 to 13:1 or about 11:1.

For purposes of the present specification, it should be understood that the term "aliquot portion" refers to both: (i) a portion of a parent stream that has the same composition as the parent stream from which it is derived, and (ii) a stream comprising a portion of a parent stream that has the same composition as the parent stream from which it is derived and one or more additional streams that have been combined therewith. Thus, directing a return stream comprising an aliquot portion 75 of the PRS distillation bottoms stream 38 to the light ends column 14 encompasses the direct transfer of a portion of the PRS distillation bottoms stream to the light ends column as well as the transfer of a derivative stream comprising (i) a portion of the PRS distillation bottoms stream and (ii) one or more additional streams that are combined therewith prior to introduction into the light ends column. An "aliquot portion" would not include, for example, streams formed in a distillation step or a phase separation step, which would not be compositionally the same as the parent stream from which they are derived nor derived from such a stream.

The vapor phase 36 from PRS distillation column 18 is cooled and condensed in receiver 20, e.g., a knock out drum. At least a portion, e.g., an aliquot portion, of resulting condensed stream 40 is directed to an extraction unit 70, in which it is extracted with an extraction agent, e.g., water, to reduce and/or remove PRC's, notably acetaldehyde. In a preferred embodiment, a portion of condensed stream 40 is refluxed as stream 42 to distillation column 18, optionally after being combined with a portion 39 of PRS distillation column bottoms stream 38 as shown in FIG. 1.

In extraction unit 70, acetaldehyde is extracted from stream 40 with the extraction agent 71, e.g., water, to reduce PRC's, notably acetaldehyde, and to obtain an extracted stream 72 comprising water, acetaldehyde, and methyl iodide. The amount of methyl iodide may vary depending on the extraction agent, extraction conditions and composition of stream 40. Thus, acetaldehyde is reduced and/or removed from the separation process. Extracted stream 72 will generally be treated as a waste, although in some embodiments acetaldehyde may be stripped, with the water being recirculated to the process, such as for the water used in extraction unit 70. The efficiency of the extraction will depend on such things as the number of extraction stages and the water to feed ratio.

Extraction with water can be either a single stage or multi stage extraction and any equipment used to conduct such extractions can be used in the practice of the present invention. Although a single stage extraction is shown in FIG. 1, multistage extraction, optionally countercurrent multistage extraction, is preferred. For example, extraction can be accomplished by combining stream 40 with water 71 and providing the combination successively to a mixer and then a separator. A suitable multiple extraction unit is described in U.S. Pat. No. 7,223,886, the entire contents and disclosure of which is hereby incorporated by reference. Combinations of mixer(s) and separator(s) can be operated in series to obtain a multistage extraction. Multistage extraction is desirably accomplished in a single vessel having a series of trays or other internals designed to facilitate efficient liquid-liquid contacting between the two phases. The vessel may be equipped with paddle(s) or other mechanisms for agitation to increase extraction efficiency. In such a multistage extraction vessel, stream 40 desirably is provided proximate to one end of the vessel with water being provided proximate to the other end of the vessel or such other location to obtain a countercurrent flow.

The mutual solubility between the two phases in the extraction can increase with temperature. Accordingly, it is desirable that the extraction be conducted at a combination of temperature and pressure such that the extractor contents can be maintained in the liquid state. Moreover, it is desirable to minimize the temperatures to which stream 40 is exposed to minimize the likelihood of polymerization and condensation reactions involving acetaldehyde. Water 71 used in the extraction unit 70 is desirably from an internal stream so as to maintain water balance within the reaction system. Dimethyl ether (DME) can be introduced to the extraction to improve the separation of methyl iodide in the extraction, i.e., to reduce the loss of methyl iodide into the extracted stream 72. Additionally or alternatively, the process conditions or PRS system may be designed such that the DME may be formed in situ. For example, in one embodiment, DME may be present in the extraction step, whether separately added or formed in situ, in an amount sufficient to reduce the methyl iodide concentration in extracted stream 72 to an amount less than 1.8 wt. %, e.g., less than 1.5 wt. %, less than 1.0 wt. % or less than 0.7 wt. %. In terms of ranges, DME may be present in the extraction step, whether separately added or formed in situ, in an amount sufficient to reduce the methyl iodide concentration in extracted stream 72 to an amount from 0.5 to 1.8 wt. %, e.g., from 0.5 to 1.5 wt. %, from 0.5 to 1.0 wt. %, or from 0.5 to 0.7 wt. %.

According to a preferred third aspect of the invention, which may be combined with either or both the first and second aspects of the invention, the raffinate 74 from the extraction, notably containing methyl iodide, desirably is returned to light ends column 14, optionally after being combined with one or more other streams, such as first portion 75, as shown. Once introduced into the light ends column, the methyl iodide from the raffinate 74 preferably exits the light ends column primarily through the overhead stream 28 and will accumulate in the heavy phase of the corresponding phase separation unit 16.

According to a fourth aspect of the invention, which may be combined with one or more of the first, second and/or third aspects of the invention, all or a portion of raffinate 74 from the extraction is returned to drying column 43, optionally after being combined with one or more other streams, such as second portion 54, as shown by dashed arrow 55. Once introduced into the drying column, the methyl iodide from the raffinate 74 preferably exits the drying column primarily through the overhead stream 44 and will accumulate in the heavy phase of the corresponding phase separation unit 46. Methyl acetate from the raffinate 74 preferably follows the same route.

In another optional embodiment, not shown, all or a portion of raffinate 74 may be added directly to decanter 16 and/or may be returned to reactor 3.

In the non-limiting embodiment shown, the raffinate in stream 74 is combined with an aliquot portion 75 of PRS distillation column bottoms stream 38 to form combined stream 76. Combined stream 76 is then added to light ends column reflux stream 34 and the resulting stream is added to the top of light ends column 14. Of course, as will be appreciated by those skilled in the art, these streams may be added to light ends column 14 in a variety of other configurations. For example, the streams may be combined in a different order or added separately to the light ends column 14.

In the present invention, the efficiency of separating acetaldehyde from methyl iodide is primarily affected by the relative solubility of acetaldehyde and methyl iodide in water. While acetaldehyde is miscible in water, methyl iodide is not. However, the solubility of methyl iodide in water increases, with a concomitant loss of methyl iodide from the process system, with increasing levels of methyl acetate and/or methanol. At high enough methyl acetate and/or methanol levels, phase separation of methyl iodide in the water extraction may not occur. Similarly, phase separation of methyl iodide in the water extraction may not occur if acetic acid concentrations are sufficiently high. Thus, it is desirable that the distillate that is condensed and provided for extraction, e.g., as stream 40, contains methanol and methyl acetate at a combined concentration of less than about 10 wt. %, more desirably less than about 5 wt. %, even more desirably less than about 2 wt. %, and even more desirably less than about 1.5 wt. %. It is desirable that the distillate that is condensed and provided for extraction contain less than about 3 wt. % acetic acid, more desirably less than about 1 wt. %, and even more desirably less than about 0.5 wt. %. Particularly desired would be acetic acid concentrations approaching 0 wt. %.

Thus, in the process of the present invention, a distillation, optionally a single distillation, is conducted in distillation column 18 under conditions designed to control, notably minimize, the quantities of methyl acetate and acetic acid in vapor phase 36. Desirably, minimization of quantities of methyl acetate and acetic acid in vapor phase 36 is achieved while simultaneously maintaining higher acetaldehyde levels in vapor phase 36 than in the residuum of distillation column 18. It is desirable that the residuum of distillation column 18 contain less than about 0.3 wt. % acetaldehyde, more desirably less than about 0.2 wt. %, and even more desirably less than about 0.1 wt. %. Particularly desired would be acetaldehyde concentrations approaching zero wt. %.

Thus, in accordance with one embodiment of the present invention, illustrated in FIG. 1, low-boiling overhead vapor stream 28 is condensed in overhead receiver decanter 16 where it is biphasically separated to form a condensed heavy liquid phase 31 and a light condensed liquid phase 30. The light condensed liquid phase 30 is provided to PRS distillation column 18 via streams 30/32. In this and other embodiments of the present invention, a portion of stream 30 can be directed back to the light ends column 14 as reflux stream 34, optionally after having been combined with either or both a portion 75, e.g., an aliquot portion, of PRS distillation column bottoms stream 38 and/or raffinate stream 74. Preferably a combined stream 76 is combined with reflux stream 34.

One of ordinary skill in the art having the benefit of this disclosure can design and operate a PRS distillation column to achieve the desired results of the present invention. Such efforts, although possibly time-consuming and complex, would nevertheless be routine for one of ordinary skill in the art having the benefit of this disclosure. Accordingly, the practice of this invention is not necessarily limited to specific characteristic of a particular distillation column or the operation characteristics thereof, such as the total number of stages, the feed point, reflux ratio, feed temperature, reflux temperature, column temperature profile, and the like.

EXAMPLE

The benefits of reduced acid recycle to the reactor according to one non-limiting embodiment of the present invention will be better understood in view of the following mass balance example.

When operating at low water composition, the methanol carbonylation unit does not consume or produce water. The reactor water composition is controlled by manipulating the flow rate of the recycle streams from the purification section back to the reactor. Therefore, at steady state, the total water contained in the recycle streams will be determined by the desired set point for reactor water composition. Using ASPEN Plus 7.1 simulation software, a comparison between a conventional process and an improved process according to the embodiment of the invention shown in FIG. 1 was determined by mass balance calculations such that the total amount of water contained in the recycle streams was the same in both cases. In this mass balance example, as shown in FIG. 1, one aliquot portion of the bottoms stream from the PRC distillation column was directed to the light ends column and second portion 54 of the bottoms stream from the PRC distillation column was directed to the drying column 43. The raffinate 74 from the extraction unit 70 was also directed to the light ends column 14.

With this assumption, the compositions of water recycle streams 41 and second portion 54 of FIG. 1 according to one embodiment of the invention were determined by mass balance and compared with streams from a conventional process where the light phase in the light ends decanter is recycled to the reactor (Stream 6). The results are shown in Table 4.

TABLE 4

|  | Flow (tons/hr) | Water (Wt. %) | Acetic Acid (Wt. %) |
|---|---|---|---|
| Conventional Process | | | |
| Stream 6 | 3.0 | 70 | 15 |
| Stream 41 | 26 | 80 | 3 |
| Stream 54 | 0 | — | — |
| Total Acid Recycle | 1.23 | | |
| Inventive Process | | | |
| Stream 6 | 0 | — | — |
| Stream 41 | 28.6 | 80 | 3 |
| Stream 54 | 2.8 | 75 | 20 |
| Total Acid Recycle | 0.858 | | |

As shown, the net result of the improved process is a decrease in the recycle rate of light phase from the light ends column and an increase in the recycle rate of the light phase from the drying column. Since the light phase of the light ends column contains a higher percentage of acetic acid than the light phase of the drying column, the improved process surprisingly and unexpectedly has 30% less acetic acid recycle than the conventional process when recycling the same total amount of water. This reduction in recycle of acetic acid is a significant benefit of the process shown in FIG. 1 and described herein over conventional processes.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. A process for removing permanganate reducing compounds (PRC's) from a crude acetic acid composition comprising acetic acid and one or more PRC's, the process comprising the steps of:
   (a) separating the crude acetic acid composition in a light ends column into a PRC enriched stream and an acetic acid stream;
   (b) separating the PRC enriched stream into an aqueous phase and an organic phase;
   (c) separating the aqueous phase in a distillation column into an overhead stream and a bottoms stream; and
   (d) directing a first return stream comprising an aliquot portion of the bottoms stream to the light ends column.

2. The process of claim 1, further comprising the step of combining the aliquot portion of the bottoms stream with one or more process streams to form the first return stream.

3. The process of claim 1, wherein the aqueous phase is separated in one or more distillation columns 4. The process of claim 1, further comprising directing the first return stream into a reflux of the light ends column.

5. The process of claim 1, further refluxing the first return stream to the light ends column 6. The process of claim 1, further comprising the step of:
   (e) extracting at least a portion of the overhead stream with an extraction medium to form a PRC extracted stream and a raffinate,
   wherein the first return stream further comprises at least a portion of the raffinate.

7. The process of claim 6, wherein the extraction medium is selected from the group consisting of water, dimethyl ether, and mixtures thereof.

8. The process of claim 7, wherein dimethyl ether is present in the extracting step in an amount sufficient to reduce methyl iodide concentration in the PRC extracted stream to an amount less than 1.8 wt.%.

9. The process of claim 7, wherein dimethyl ether is present in the extracting step in an amount sufficient to reduce methyl iodide concentration in the PRC extracted stream to an amount less than 1.0 wt.%.

10. The process of claim 7, wherein dimethyl ether is present in the extracting step in an amount sufficient to reduce methyl iodide concentration in the PRC extracted stream to an amount from 0.5 to 1.8 wt.%.

11. The process of claim 7, further comprising the steps of:
    (f) distilling the acetic acid stream in a drying column to form a water stream and an acetic acid product stream; and
    (g) directing a second return stream comprising an aliquot portion of the bottoms stream to the drying column.

12. The process of claim 11, wherein the second return stream further comprises an aliquot portion of the raffinate, a reflux stream of the drying column, or a combination thereof.

13. The process of claim 1, further comprising the steps of:
    (e) distilling the acetic acid stream in a drying column to form a water stream and an acetic acid product stream; and
    (f) directing a second return stream comprising an aliquot portion of the bottoms stream to the drying column.

14. The process of claim 13, further comprising the step of:
    (g) extracting at least a portion of the overhead stream with an extraction medium to form a PRC extracted stream and a raffinate,
    wherein the second return stream further comprises a portion of the raffinate.

15. The process of claim 1, further comprising the steps of:
    (e) extracting at least a portion of the overhead stream with an extraction medium to form a PRC extracted stream and a raffinate;
    (f) distilling the acetic acid stream in a drying column to form a water stream and an acetic acid product stream; and
    (g) directing a second return stream comprising an aliquot portion of the raffinate to the drying column.

16. A process for removing permanganate reducing compounds (PRC's) from a crude acetic acid composition comprising acetic acid and one or more PRC's, the process comprising the steps of:
    (a) separating the crude acetic acid composition in a light ends column into a PRC enriched stream and an acetic acid stream;
    (b) separating the PRC enriched stream into an aqueous phase and an organic phase;
    (c) separating the aqueous phase in a distillation column into an overhead stream and a bottoms stream;
    (d) extracting at least a portion of the overhead stream with an extraction medium in an extraction unit to form a PRC extracted stream and a raffinate; and
    (e) directing a first return stream comprising an aliquot portion of the raffinate to the light ends column.

17. The process of claim 16, wherein the extraction medium is selected from the group consisting of water, dimethyl ether, and mixtures thereof.

18. The process of claim 16, further comprising the step of combining the aliquot portion of the raffinate with one or more process streams to form the first return stream.

19. The process of claim 16, wherein at least a portion of the bottoms stream is directed to the light ends column, optionally as part of the first return stream.

20. The process of claim 16, further comprising the steps of:
(f) distilling the acetic acid stream in a drying column to form a water stream and an acetic acid product stream; and
(g) directing a second return stream comprising an aliquot portion of the bottoms stream to the drying column.

21. The process of claim 20, wherein the second return stream comprises the aliquot portion of the bottoms stream and a reflux stream.

22. The process of claim 16, wherein the first return stream further comprises an aliquot portion of the bottoms stream.

23. A process for removing permanganate reducing compounds (PRC's) from a crude acetic acid composition comprising acetic acid and one or more PRC's, the process comprising the steps of:
(a) separating the crude acetic acid composition in a light ends column into a PRC enriched stream and an acetic acid stream;
(b) separating the PRC enriched stream into an aqueous phase and an organic phase;
(c) separating the aqueous phase in a distillation column into an overhead stream and a bottoms stream;
(d) distilling the acetic acid stream in a drying column to form a water stream and an acetic acid product stream; and
(e) directing a first return stream comprising an aliquot portion of the bottoms stream to the drying column.

24. The process of claim 23, wherein the first return stream comprises the aliquot portion of the bottoms stream and a reflux stream.

25. The process of claim 23, further comprising the step of:
(f) extracting at least a portion of the overhead stream with an extraction medium to form a PRC extracted stream and a raffinate,
wherein the first return stream further comprises an aliquot portion of the raffinate.

26. The process of claim 25, wherein the extraction medium is selected from the group consisting of water, dimethyl ether, and mixtures thereof.

27. The process of claim 23, further comprising the steps of:
(f) extracting at least a portion of the overhead stream with an extraction medium to form a PRC extracted stream and a raffinate; and
(g) directing a second return stream comprising an aliquot portion of the raffinate to the light ends column.

28. A process for removing permanganate reducing compounds (PRC's) from a crude acetic acid composition comprising acetic acid and one or more PRC's, the process comprising the steps of:
(a) separating the crude acetic acid composition in a light ends column into a PRC enriched stream and an acetic acid stream;
(b) separating at least a portion of the acetic acid stream in a drying column to form a water stream and an acetic acid product stream;
(c) separating the PRC enriched stream into an aqueous phase and an organic phase;
(d) separating the aqueous phase in a distillation column into an overhead stream and a bottoms stream;
(e) extracting at least a portion of the overhead stream with an extraction medium to form a PRC extracted stream and a raffinate;
(f) directing a first return stream comprising an aliquot portion of the bottoms stream to the light ends column;
(g) directing at least a portion of the raffinate to the light ends column, optionally as part of the first return stream; and
(h) directing a second return stream comprising an aliquot portion of the bottoms stream to the drying column.

* * * * *